United States Patent [19]

Stolle

[11] Patent Number: 5,130,128
[45] Date of Patent: Jul. 14, 1992

[54] USE OF HONEY AS VACCINE

[75] Inventor: Ralph J. Stolle, Oregonia, Ohio

[73] Assignee: Stolle Research & Development Corporation, Cincinnati, Ohio

[21] Appl. No.: 431,639

[22] Filed: Nov. 6, 1989

Related U.S. Application Data

[60] Continuation-in-part of Ser. No. 161,039, Feb. 26, 1988, Pat. No. 4,879,110, which is a continuation-in-part of Ser. No. 1,848, Jan. 9, 1987, Pat. No. 4,897,265, which is a division of Ser. No. 546,162, Oct. 27, 1983, Pat. No. 4,636,384, which is a continuation-in-part of Ser. No. 384,625, Jun. 3, 1982, abandoned.

[51] Int. Cl.$^5$ ............................................. A61K 39/395
[52] U.S. Cl. .................................................... 424/85.8
[58] Field of Search ............................. 424/85.8, 88, 87

[56] References Cited

U.S. PATENT DOCUMENTS

| | | | |
|---|---|---|---|
| 3,128,230 | 4/1964 | Heinbach | 167/78 |
| 3,376,198 | 4/1968 | Peterson et al. | 167/78 |
| 3,911,108 | 10/1975 | Singh | 424/86 |
| 4,284,623 | 8/1981 | Beck | 424/85 |
| 4,324,782 | 4/1982 | Beck | 424/87 |
| 4,357,272 | 11/1982 | Polson | 260/112 |
| 4,550,019 | 10/1985 | Polson | 424/85 |
| 4,636,384 | 1/1987 | Stolle et al. | 424/87 |
| 4,732,757 | 3/1988 | Stolle et al. | 424/87 |
| 4,748,018 | 5/1988 | Stolle et al. | 424/87 |
| 5,080,895 | 1/1992 | Tokoro | 424/85.8 |

FOREIGN PATENT DOCUMENTS 1211876 11/1970 United Kingdom .
1442283 7/1976 United Kingdom .

OTHER PUBLICATIONS

Jensenius, J. C. et al., *Journal of Immunological Methods* 46:363–368 (1981).
Polson, A. et al., *Immunological Communications* 9:475–493 (1980).
LeBacq-Verheyden, A. M. et al., *Immunology* 27:683–692 (1974).
Polson, A. et al., *Immunological Communications* 9:495–514 (1980).
Fertel, R. et al., *Biochemical and Biophysical Research Communications* 102:1028–1033 (1981).
Miedzobrodza, A. et al., *Przegl. Lek.* 34:721–724 (1977).
Bonneau, J. C. et al., *Allerg. Immunol.* 17:526–527 (1985).
Spika, J. S. et al., *Am. J. Dis. Child.* 143:828–832 (1989).

*Primary Examiner*—Peter D. Rosenberg
*Attorney, Agent, or Firm*—Sterne, Kessler, Goldstein & Fox

[57] ABSTRACT

Anti-honey food products are disclosed, such food products being obtained from animals hyperimmunized against at least one antigen found in honey, and preferably whole unfractionated honey. A vaccine producing said anti-honey food product is disclosed, said vaccine comprising at least one honey antigen and preferably whole unfractionated honey. Further, a dietary supplement for humans and especially infants which protects against harmful allergens and microorganisms found in honey is disclosed, said supplement comprising the anti-honey eggs or milk or fractions thereof.

13 Claims, No Drawings

USE OF HONEY AS VACCINE

CROSS-REFERENCES TO RELATED DOCUMENTS

The present application is a continuation-in-part of Ser. No. 161,039, now U.S. Pat. No. 4,879,110, filed Feb. 26, 1988 which is a continuation-in-part of Ser. No. 001,848, filed Jan. 9, 1987, now U.S. Pat. No. 4,897,265, which is a division of Ser. No. 546,162 filed Oct. 27, 1983, now U.S. Pat. No. 4,636,384, which is a continuation-in-part of application Ser. No. 384,625, filed Jun. 3, 1982, now abandoned.

BACKGROUND OF THE INVENTION

1. Field of the Invention

This invention relates to the use of honey and/or bee as a component of a vaccine for immunizing cows and/or chickens against the allergens and microorganisms contained therein. The invention further relates to food products such as milk and/or eggs from animals hyperimmunized against honey and/or the bee, and to the use of such food products, as a source of anti-honey factors which protect a host which ingests such food products against the allergens and microorganisms found in honey.

2. Description of the Background Art

The body of the bee, more specifically the hind legs, is used to collect pollen that is used as a food by the bees in the hive. Many of the pollens are allergens. These are the same allergens (for example, ragweed) that cause environment-related allergic reactions in humans or other animal species living in the area. As a result, honey made by the bee, and the body of the bee, carry a random sample of various pollens and other allergens or microorganisms that are indigenous to a specific geographical area. Bees and honey from different geographical areas carry different kinds of pollen because the vegetation varies.

The allergic properties of honey have been described. (Miedzobrodza, A. et al., *Przegl. Lek.* 34:721–724 (1977); Bonneau, J. C. et al., *Allerg. Immunol.* 17:526–527 (1985)). In susceptible individuals honey can induce bronchial asthma attacks, and allergic and antibody-mediated hypersensitivity reactions, such attacks may be severe and be accompanied by tissue damage.

Young infants are unusually susceptible to toxic microorganisms in honey. For a food product, honey provides an unusually concentrated source of spores of *Clostridium botulinum*, the microorganism responsible for botulism. *Clostridium botulinum* has been estimated to contaminate 10–15% of all honey. (Brown, L. W., *J. Pediatr.* 94:337–338 (1979); Spika, J. S. et al., *Am. J. Dis. Child.* 143:828–832 (1989)). Unfortunately, honey is often used as an alternative to cane sugar in infant formula preparations and infant botulism is now the most common form of botulism identified in this country.

Honey is the only food source thus far implicated in the pathogenesis of infant botulism. Approximately 15% of the infant botulism cases identified in the United States are associated with ingestion of honey (Spika, J. S. et al., *Am. J. Dis. Child.* 143:828–832 (1989); Hauschild, A. H. W. et al. *J. Food Prot.* 51:892–894 (1988)). Infant botulism may also arise due to ingestion or inhalation of the *C. botulinum* spores from environmental exposure to dust or dirt. When ingested, toxin is formed within the gut of the infant after the germination and multiplication of the *C. botulinum* spores.

Release of botulism toxin in adults and especially in infants and children can be fatal. Treatment of botulism in infants is merely supportive. Thus, it would be advantageous to have a method for the treatment or prevention of infant botulism.

It has been known in the prior art to produce milk having a variety of therapeutic effects. Beck, for example, has disclosed a milk containing antibody to *Streptococcus mutans* that has dental caries-inhibiting effects (Beck, U.S. Pat. No. 4,324,782; British Patent 1,505,513). The milk is obtained by hyperimmunization of a cow with *Streptococcus mutans* antigen and collecting the therapeutic milk therefrom. Beck has also described a milk having anti-arthritic properties (U.S. Pat. No. 4,732,757), and has patented a method of treating inflammation using milk from hyperimmunized cows (Beck, U.S. Pat. No. 4,284,623). Stolle has disclosed a method of using milk from a hyperimmunized cow to treat diseases of the vascular and pulmonary systems (Stolle et al., U.S. Pat. No. 4,636,384). Heinbach, U.S. Pat. No. 3,128,230, has disclosed milk containing alpha, beta and gamma globulins against anti-9-enic haptens. Singh (U.S. Pat. No. 3,911,108), Peterson (U.S. Pat. No. 3,376,198 and Canadian Patent 587,849), Holm (U.S. application (published) Ser. No. 628,987), Tunnah et al. (British Patent 1,211,876), and Biokema S. A. (British Patent 1,442,283) have also described antibody-containing milks.

In U.S. Pat. Nos. 4,636,384, and 4,897,265, there was disclosed a method of lowering blood lipid levels and treating lipid-associated vascular disorders, as well as treating macrophage-related pulmonary disorders, comprising feeding test animals and humans antibody-containing milk derived from cows maintained in a hyperimmune state by injections of polyvalent antigens derived from mixtures of killed bacteria. In allowed application Ser. No. 07/355,786, filed May 22, 1989, and which is a file wrapper continuation of U.S. Ser. No. 069,139, filed Jul. 2, 1987, now abandoned, there was disclosed use of antibody-containing milk derived from hyperimmunized cows for the treatment of gastrointestinal disorders.

It is well known to those skilled in the art of immunology that serum globulin fractions consisting of various antibody types such as, for example, IgA, IgG, and IgM, can be used to counter corresponding antigens, thereby neutralizing the effects of the antigens. There are an almost infinite number of harmful antigens to which animals can be exposed, including carcinogenic, bacterial, viral, and regulatory factors of plant and animal origin, as well as toxins and poisons.

Normally, upon exposure to a foreign antigen, e.g., pollen, the immune system of the host will produce antibodies that will neutralize the effects of the antigen. Exposure to such foreign antigens can occur either naturally, or deliberately by administration of the antigen in vaccine form. The latter is generally referred to as active immunization of the host species exposed to the antigen. The antibodies produced in response to such vaccination are homologous to said given species of animal, and are epitopic to the antigen.

It is known that various genera of the class Aves, such as chickens (*Gallus domesticus*), turkeys, and ducks, produce antibodies in their blood and in their eggs against factors which cause avian diseases, as well as against other antigens. For example, LeBacq-Verheyden et al., *Immunology* 27:683 (1974), and Nestle, G. A. et al., *J. Med.* 130:1337 (1969), have quantitatively analyzed immunoglobulins of the chicken. Polson, A. et al., *Immunological Communications* 9:495-514 (1980) immunized hens against several proteins and natural mixtures of proteins, and detected IgY antibodies in the yolks of the eggs. Fertel, R. et al., *Biochemical and Biophysical Research Communications* 102:1028-1033 (1981) immunized hens against prostaglandins and detected antibodies in the egg yolk. Jensenius et al., *Journal of Immunological Methods* 46:363-368 (1981), provide a method of isolating egg yolk IgG for use in immunodiagnostics. Polson et al., *Immunological Communications* 9:475-493 (1980), describe antibodies isolated from the yolk of hens that were immunized with a variety of plant viruses.

Polson, U.S. Pat. No. 4,357,272, discloses the isolation of antibodies from the yolks of eggs derived from hyperimmunized hens. The hyperimmunization was elicited by repetitive injections into the hens of antigens represented by plant viruses, human IgG, tetanus antitoxin, snake antivenins, and Serameba antigens. Polson, U.S. Pat. No. 4,550,019, discloses the isolation from egg yolks of antibodies raised in the hen by hyperimmunization with immunogens having a molecular or particle weight of at least 30,000. The antigens used to hyperimmunize the chickens were selected from among plant viruses, human immunoglobulins, tetanus toxin, and snake venoms.

In Ser. No. 577,804, there is disclosed a method of passive immunization of a mammal which comprises parenterally injecting a purified heterologous antibody obtained from the eggs of a domesticated fowl, which species has been immunized against an antigenic substance, and wherein the mammal has a history of consumption of eggs from such domesticated fowl. The invention disclosed in U.S. Pat. No. 4,748,018 expands on the concepts disclosed in U.S. Ser. No. 577,804, in that administration of the egg antibody can be any appropriate route, not only parenteral.

The present invention is a further development over the inventions disclosed and claimed in the aforementioned applications, the entire disclosures of which are herein incorporated by reference.

SUMMARY OF THE INVENTION

It is an object of the invention to produce food products, and specifically avian eggs and bovine milk which, when consumed by humans and other warm-blooded animals, will protect such animals against the damage caused by allergens, toxic microorganisms and other antigens found in honey.

It is also an object of the invention to provide a method of treating or protecting human infants against the effects of ingested spores of *C. botulinum*.

The invention provides materials and a process for producing such food products, and especially such avian eggs and bovine milk, such materials comprising honey and/or bee antigens in vaccine form, and such process comprising immunization and hyperimmunization of avians and bovines with said antigen vaccine.

These and other objects of the invention, which will hereinafter become more readily apparent, have been obtained by providing honey and/or bee as a vaccine for immunizing bovines and chickens. The methods of the invention comprise administering to an animal which is susceptible to allergens, antigens or toxins found in honey, egg products collected from avian genera maintained in a hyperimmune state against honey antigens and/or milk products from bovine genera maintained in hyperimmune state against honey antigens. Upon consumption by the animal being treated, the food products of the invention protect against tissue damage induced by the inhalation or consumption of honey allergens, antigens or toxins.

DETAILED DESCRIPTION OF THE PREFERRED EMBODIMENTS

As used hereinafter, the terms "anti-honey allergen egg(s)" or "anti-honey allergen milk" refer to the avian eggs or bovine milk respectively, of the present invention, said eggs or milk produced by maintaining the avian or bovine animal in a hyperimmune state against the specific class of antigenic materials found in honey or on the outer surface of the bee's coat or legs. The term "honey antigen(s)", as used hereinafter, shall mean those antigens derived from bee honey and/or the honeybee. Especially, the term "honey antigens" refers to pollens and microorganisms which can be extracted from honey or which are carried by the bee to the hive on its coat or legs. As used hereinafter the term "vaccine" refers to a suspension of honey and/or honeybee or some antigenic pollen-containing fraction thereof which, when administered to an avian or bovine, results in the production of antibodies against said antigen. (Davis, B. D. et al., *Microbiology*, 3rd ed., 1980, at p. 294).

The invention comprises a natural food product (anti-honey eggs and/or anti-honey milk) which has beneficial immunological and tissue protection properties towards animals which ingest it, as well as a method for producing and using the same. The anti-honey eggs and milk of the present invention, being natural products, can be used to prevent the allergic reactions and toxic responses associated with inhalation or ingestion of honey allergens, antigens or toxins without fear of side effects.

In the process of this invention, the source animal includes any milk-producing animal of the genus Bos, preferably but not limited to the domesticated cow, and any egg-producing member of the class Aves, preferably, but not limited to, domesticated chickens (genus *Gallus domesticus*). Accordingly, the genera represented by cows and the like may be used as the source of the hyperimmune milk, and genera represented by turkeys, ducks, geese, and the like may be used as the source of the hyperimmune eggs.

The invention is based on the discovery that when such avians or bovines are brought to a specific state of immunization by means of periodic booster administrations of the specific class(es) of antigen contained in honey, or found on the body of the bee, or a mixture of such antigens, the animal will produce food products such as eggs or milk which, when consumed, have beneficial properties in the treatment of allergic, immunological and toxic effects of exposure to such antigens, whether such exposure occurs due to inhalation of the antigen from the environment, or to ingestion of the antigen in a food source. The food products of the invention which contain these beneficial properties include eggs and milk from animals hyperimmunized with such honey and/or bee antigens and are herein called "anti-honey" eggs and "anti-honey milk."

The beneficial immunological and toxicological properties of the food products of the invention are called herein "anti-honey" properties and are not produced by all avians or bovines that are simply immunized. That is to say, the induction of immune sensitivity alone is insufficient to cause the appearance of the aforementioned anti-honey properties in eggs and milk, as is shown by the fact that normal fowl eggs or bovine milk do not contain these properties, even though fowl and bovines have become sensitized against various antigens during normal immunization against fowl and bovines diseases.

Furthermore, the properties are not always present in eggs or milk produced by fowl or bovines maintained in the immune state by booster injection. It is only in a specific hyperimmune state that the eggs or milk produced have the desired effect. This special state is achieved only by administering periodic boosters with sufficiently high doses of specific honey antigens or mixtures of such antigens. The preferred dose range should be equal to or greater than 50% of the dosage necessary to cause primary sensitization of the avian or bovine. Having knowledge of the requirement for developing and maintaining a hyperimmune state, it is within the skill of the art to vary the amount of honey antigen administered, depending upon the avian or bovine genera and strain employed, in order to maintain the animal in the hyperimmune state.

In summary, the process comprises the following steps:

1. Selection of the honey and/or bee as a source of antigens.
2. Sensitization of avians or bovines by primary immunization.
3. Administering boosters of honey and/or bee antigens of appropriate dosage to induce and maintain a hyperimmune state.
4. Collecting eggs or milk from the animal during the hyperimmune state.
5. Testing anti-honey properties of eggs or milk collected from said hyperimmune avian or bovine.

Step 1—Selection of the honey and/or bee as a source of antigens. The avian or bovine is immunized and hyperimmunized with a specific anti-honey vaccine which contains the honey and/or bee antigens. In a preferred embodiment whole honey is used in an unfractionated form. The high viscosity of the honey, due to the high concentration of sugar, may aid the immunization process by acting as an adjuvant for the antigens contained therein. In another embodiment bees, or the coats or legs thereof, or extracts containing washings from the coats or legs of bees, are used in the vaccine. The avian responds to administration of this vaccine by producing antibodies in the eggs, against the immunogens in the honey or from the bee used for the immunization; the bovine responds to administration of this vaccine by producing antibodies in the milk against the immunogens in the honey or from the bee used for the immunization. Immunological factors such as specific egg antibodies or specific milk antibodies, produced in response to the immunization, result in the anti-honey factors which provide the beneficial properties to the food products of the invention.

Step 2—Honey or bee antigens can be administered by any method which causes sensitization. The preferred method of immunization is by intramuscular injection. The preferred method of administration of the antigens to chickens is in the breast muscle. The dosage is preferably 1-5 mg of the honey or bee vaccine. Repeated immunizations are given at intervals, preferably two-week, over a suitable period of time, preferably six months.

It can be determined whether or not the animal has become sensitive to the antigen. There are a number of methods known to those of skill in the art of immunology to test for sensitivity. *Methods in Immunology and Immunochemistry*, Williams, C. A., Chase, W. N., Academic Press, N.Y., London (Vols. 1-5) (1977). The appearance of antibodies in the egg or milk after immunization with the vaccine is indicative of sensitivity. The minimum dose of antigen necessary to induce hypersensitivity depends on the type of antigen used.

Step 3 involves the induction and maintenance of the hyperimmune state. This state is induced by repeated booster administration of an appropriate dosage at fixed-time intervals, preferably two-week intervals over a six-month period of time where honey or bee antigens are employed. Moreover, the booster administration must not induce a state of immune tolerance. This will cause the animal to pass from a hyperimmune state to a state of immune tolerance to the antigen, in which case the animal will cease to produce food products such as milk or eggs with the beneficial properties.

It might also be possible, for example, to use a combination of different immunization procedures, i.e., intramuscular injection for primary immunization and intravenous injection for booster injections, etc. Many different combinations of immunization might be employed by those skilled in the arts to: (1) sensitize and (2) induce the hyperimmune state.

Step 4 involves collection and processing of the eggs or milk. If the eggs or milk are to be processed into dried egg or dried milk powders, freeze-drying (lyophilization) is the preferred method. Whole eggs or milk can also be used, as well as eggs that have been separated into egg yolks and egg white and skim milk. The beneficial factors, including the beneficial antibodies are present in the egg yolk.

Step 5 is to test the ability of the anti-honey food products to prevent tissue damage caused by antigen-induced allergic responses. Such properties can be demonstrated by studying the effect of feeding the milk or eggs of the invention to animal models exposed to antigens which induce such tissue damage. The common white laboratory rat is the preferred model. Laboratory rats kept under controlled laboratory conditions and fed normal rat food can easily be exposed to antigens which promote the type of tissue damage prevented by ingestion of the food products of the invention. The preferred method of exposure to induce such tissue damage is to administer the antigen in an aerosol form. For example, one model system which may be used is to expose the rat to smoke which contains such antigens. Inhaled smoke which contains damaging antigens results in damage to the lung tissue which is a direct result of the allergic response to the antigens in the smoke. Such tissue damage to the lungs can be revealed by histological examination of the lungs.

The protective properties of the food products of the invention are tested by feeding the food product, for example, the anti-honey milk and/or anti-honey egg, to the rats that are exposed to antigen-containing smoke in this manner. The inventor has discovered that smoke produced by the combustion of tobacco products, i.e. cigarette smoke, contains antigens which induce an allergic reaction in rat lung which is prevented by the food products of the invention when such food products contain the above-described anti-honey protective factors.

The food products of the invention can be provided in any amount which, in warm blooded animals, effects (brings about or induces) the reversal of tissue damage or toxicological interactions caused by honey antigens and microorganisms. Such effect may also consist of a prevention of the occurrence of such damage in the first place, or of maintaining such a preventive effect. An animal being administered the food products of the invention in a manner which provides efficacious amounts of the anti-honey protective factors so as to effect a reversal of such tissue damage, or prevent an occurrence of such tissue damage or maintain a preventive effect against the occurrence of such tissue damage, is said to be being "treated" according to the methods of the invention.

The same amounts can be utilized in subjects when the food products of the invention are ingested so as to provide a preventive effect against subsequent exposure to antigens contained in honey or carried on the bee. The food products of the invention, such as whole eggs or whole milk or egg yolks or skim milk, can be incorporated into any food product, as long as the food product is not treated at a temperature which is too elevated and which would thereby inactivate the beneficial anti-honey properties of the product.

Further, it has been found that the yolk fractions of eggs contain the agent or agents responsible for the beneficial properties observed and referred to above. Those of ordinary skill in the art, knowing that the yolk fraction contains the factors of importance, would clearly recognize that further separation can be made to obtain more potent fractions.

The preferred dose of the anti-honey milk is 50 grams of milk powder reconstituted in 8 oz. of water taken once daily. The effective dose may very among individuals from approximately 25 to 100 grams. One quart of fresh whole anti-honey milk contain approximately 90 grams of solids. The milk may be converted into a powder by any technique commonly employed in the art, provided that the process does not involve heating the milk to such a temperature that would destroy the beneficial anti-honey properties.

The preferred dose of the anti-honey egg is the antibody equivalent of one whole egg yolk taken once daily. The effective dose may vary among individuals from ¼ of an egg to 3 eggs. The antibody content of one whole egg is approximately 15 milligrams.

The food products of the invention, anti-honey avian egg and anti-honey bovine milk may be incorporated into infant formula as infant food, so as to provide to infants who ingest this formula, and especially to infants less than two months old, the beneficial anti-honey properties and especially those anti-honey properties which confer protection against the ingested spores of *Clostridium botulinum*. An advantage of such administration is that the protective factors are administered to the infant or child in a food product such as milk which is usually tolerated by the infant or child. It is also an advantage that by ingesting the protective factors, such protective factors are administered directly into the intestinal tract of the infant or child.

Having now generally described this invention, the same will be further described by reference to certain specific examples which are provided herein for purposes of illustration only and are not intended to be limiting unless otherwise specified.

EXAMPLE 1

Immunization Against Honey Antigens

Bee honey contains a diverse group of antigens, the exact composition of which is unknown. The antigen in honey is capable of inducing a hyperimmune state when injected in cows.

Cows were immunized once a week, intramuscularly, for three weeks, then at two week intervals for an additional two to three months. A single dose consists of 2.5 ml sterile distilled water and 2.5 ml raw honey. Milk was collected for the two weeks following the final injection.

In another example a dose of 1 ml of honey diluted 1:5 in water was injected into the chicken breast muscle, one a week for five consecutive weeks, then once every two weeks for six months.

Eggs collected between the third and sixth months and tested for antibody were able to induce and maintain the hyperimmune state in the animal.

Bovines and avians may also be immunized with homogenized bee, or with washings of the coats of bees, in a similar manner.

EXAMPLE 2

Anti-Honey of Anti-Bee Milk Protects Lung Tissue From Damage Induced by Antigens in Cigarette Smoke Forty-one adult female Charles Rivers rats were used for this study. All rats received Wayne Rodent Laboratory Chow ad libitum. Three times daily they were exposed to cigarette smoke (30 minutes/exposure). The experiment lasted three months.

Rats were divided into five groups. Group I (7 rats) received water to drink. Group II (7 rats) received regular skim milk which had been pasteurized under conditions of low temperature (U.S. Pat. No. 4,879,110), that is, under conditions which did not raise the pasteurization temperature so high as to inactivate the beneficial components of the milk of the invention. Such pasteurization is herein called special pasteurization. Group III (9 rats) drank conventionally pasteurized anti-honey skim milk. Conventionally pasteurized milk is heated at a temperature which destroys the beneficial components of the milk of the invention. Group IV (9 rats) received specially pasteurized anti-honey skim milk. Group V (9 rats) received specially pasteurized anti-bee skim milk.

Water for rats in Group I, and the above-described milk products for rats in Groups II through V, was available ad libitum. Liquids were changed twice daily. The animals drank from sterilized bottles fitted with stainless steel drinking tubes.

After three months, all rats were sacrificed. Each rat was injected into the peritoneal cavity with an overdose of nembutal. Thoracic and cervical viscera were exposed, and a blood sample was taken from the heart. A hemostat was clamped over the trachea at the inferior border of the larynx. A 23 gauge hypodermic needle was inserted into the trachea and a fixative of 1% glutaraldehyde and 1% paraformaldehyde (pH 7.3) was infused into the tracheal lumen. This method of fixation was used in an attempt to preserve the trachea and lungs as close to the "living state" as possible.

After the pulmonary tissue had hardened, it was processed further by standard techniques for viewing in the scanning electron microscope. Particular attention was given to the tracheal epithelium and to the intrapulmonary bronchi and other air tubes as far as the respiratory bronchioles. With the scanning electron microscope, specimens could be viewed at magnifications ranging from 10× to 50,000×.

It was readily apparent that the cigarette smoke caused severe metaplasia to the lining epithelium in the tracheas of rats in Group I (water, Group II (specially pasteurized regular skim milk), and Group III (conventionally pasteurized anti-honey skim milk). As much as 100% of the tracheal epithelium in these rats was damaged. In contrast, the tracheal epithelium of rats in Group IV (specially pasteurized anti-bee milk) manifested a very high degree of protection. Even under the severe conditions of smoke inhalation used in these studies, there was little damage to the tracheal epithelium in most rats of Groups IV and V, and no damage at all to the tracheal epithelium in several of the rats.

It was concluded that the tracheal epithelium in rats of Groups IV and V was protected by some special component in the milk that the rats drank. This substance was not present in regular milk that was specially pasteurized (rats in Group II), or in conventionally pasteurized anti-honey milk (rats in Group III), and it was not present in the water or solid diet consumed by the rats (rats in Group I).

The cigarette smoke also affected the epithelium of the bronchi and intrapulmonary air passages through the respiratory bronchioles in much the same manner as it did the tracheal epithelium. Rats in Group IV and V received protection, and rats in Groups I, II, and III did not receive protection.

Now having fully described this invention, it will be understood by those with skill in the art that the scope may be performed within a wide and equivalent range of conditions, parameters, and the like, without affecting the spirit or scope of the invention or any embodiment thereof.

What is claimed and intended to be covered by Letters Patent of the United States is:

1. Avian egg produced by a process comprising: immunizing a female avian with honey; maintaining said female avian in a hyperimmune state by administering to said female avian booster injections of said honey; and collecting eggs from said avian in a hyperimmune state.

2. Bovine milk produced by a process comprising: immunizing a cow with honey: maintaining said cow in a hyperimmune state by administering to said cow booster injections of said honey: and collecting milk from said cow in a hyperimmune state.

3. A food product comprising said egg of claim 1 or said milk of claim 2.

4. A method for producing an egg comprising:
immunizing a female avian with honey;
maintaining said female avian in a hyperimmune state by administering to said female avian booster injections of said honey; and
collecting eggs from said avian in a hyperimmune state.

5. The method of claim 4 wherein said female avian is a female chicken.

6. A method for producing milk comprising:
immunizing a cow with honey;
maintaining said cow in a hyperimmune state by administering to said cow booster injections of said honey; and
collecting milk from said cow in a hyperimmune state.

7. A method of preventing tissue injury which occurs in response to allergic or toxic reactions induced by honey allergens in a warm-blooded animal which comprises administering to said animal a food product produced by the process of immunizing a female avian or bovine with honey, maintaining said female in a hyperimmune state by administering to said female booster injections of honey, and collecting either eggs or milk from said female in a hyperimmune state, in an amount and for a time sufficient to produce an anti-allergic or anti-toxic effect.

8. The method of claim 7, wherein said food product is selected from the group consisting of avian egg, avian egg yolk, bovine milk and bovine skim milk.

9. The method of claim 7, wherein said food product is in powdered form.

10. The method of claim 7, wherein said food product is in liquid form.

11. The method of claim 7, wherein said warm-blooded animal comprises humans.

12. The method of claim 11, wherein said human is an infant less than two months old.

13. The method of claim 12, wherein said anti-allergic or anti-toxic reaction confers protection against *Clostridium botulinum*.

* * * * *